(12) United States Patent
Wang et al.

(10) Patent No.: US 10,494,520 B2
(45) Date of Patent: Dec. 3, 2019

(54) BENZOXAZINE LOW TEMPERATURE CURABLE COMPOSITION

(71) Applicant: Huntsman Advanced Materials Americas LLC, The Woodlands, TX (US)

(72) Inventors: Dong Wang, The Woodlands, TX (US); Bradley Rechichar, The Woodlands, TX (US); Derek S. Kincaid, Spring, TX (US); Ronald C. Smith, Jr., Conroe, TX (US)

(73) Assignee: HUNTSMAN ADVANCED MATERIALS AMERICAS LLC, The Woodlands, TX (US)

( * ) Notice: Subject to any disclaimer, the term of this patent is extended or adjusted under 35 U.S.C. 154(b) by 0 days.

(21) Appl. No.: 15/554,858

(22) PCT Filed: Mar. 4, 2016

(86) PCT No.: PCT/US2016/020800
§ 371 (c)(1),
(2) Date: Aug. 31, 2017

(87) PCT Pub. No.: WO2016/141257
PCT Pub. Date: Sep. 9, 2016

(65) Prior Publication Data
US 2018/0030264 A1    Feb. 1, 2018

Related U.S. Application Data

(60) Provisional application No. 62/127,866, filed on Mar. 4, 2015.

(51) Int. Cl.
| | | |
|---|---|---|
| C08L 61/34 | (2006.01) | |
| C07D 265/14 | (2006.01) | |
| C08J 5/04 | (2006.01) | |
| C08G 14/06 | (2006.01) | |
| C09D 161/06 | (2006.01) | |
| C09D 161/34 | (2006.01) | |
| C09J 161/06 | (2006.01) | |
| C09J 161/34 | (2006.01) | |
| C08L 61/06 | (2006.01) | |
| C07D 413/14 | (2006.01) | |
| C07D 265/16 | (2006.01) | |
| C08J 5/24 | (2006.01) | |
| C08K 5/34 | (2006.01) | |
| C08G 73/22 | (2006.01) | |

(52) U.S. Cl.
CPC ............ *C08L 61/34* (2013.01); *C07D 265/14* (2013.01); *C07D 265/16* (2013.01); *C07D 413/14* (2013.01); *C08G 14/06* (2013.01); *C08G 73/22* (2013.01); *C08J 5/04* (2013.01); *C08J 5/043* (2013.01); *C08J 5/24* (2013.01); *C08K 5/34* (2013.01); *C08L 61/06* (2013.01); *C09D 161/06* (2013.01); *C09D 161/34* (2013.01); *C09J 161/06* (2013.01); *C09J 161/34* (2013.01); *C08J 2361/34* (2013.01); *C08J 2379/00* (2013.01); *C08J 2461/06* (2013.01); *C08J 2463/04* (2013.01); *C08L 2201/08* (2013.01); *C09J 2461/00* (2013.01); *C09J 2463/00* (2013.01)

(58) Field of Classification Search
CPC ...... C08L 61/34; C07D 265/14; C07D 265/16
USPC .......................................................... 544/90
See application file for complete search history.

(56) References Cited

U.S. PATENT DOCUMENTS

| | | |
|---|---|---|
| 4,607,091 A | 8/1986 | Schreiber |
| 5,021,484 A | 6/1991 | Schreiber et al. |
| 5,200,452 A | 4/1993 | Schreiber |
| 5,443,911 A | 8/1995 | Schreiber et al. |
| 6,207,786 B1 | 3/2001 | Ishida et al. |
| 6,376,080 B1 | 4/2002 | Gallo |
| 2009/0181165 A1* | 7/2009 | Liang ............... C08G 59/245 427/99.4 |
| 2011/0189458 A1 | 8/2011 | Sudo et al. |
| 2012/0129414 A1 | 5/2012 | Chang et al. |
| 2013/0266737 A1 | 10/2013 | Sudo et al. |

FOREIGN PATENT DOCUMENTS

WO    2008034753 A1    3/2008

OTHER PUBLICATIONS

Supplementary European Search Report dated Sep. 27, 2018, issued in the prosecution of European Patent Application No. 16759547.9, filed Aug. 31, 2017, 6 pages.

C. Jubsilpa et al., "Property Enhancement of Polybenzoxazine Modified with Dianhydride", Polymer Degradation and Stability, 96, 1047-1053, 201.

* cited by examiner

*Primary Examiner* — Kahsay Habte
(74) *Attorney, Agent, or Firm* — Huntsman Advanced Materials Americas LLC; Monique Raub

(57) ABSTRACT

The present disclosure provides an organic sulfur acid-free composition containing a benzoxazine, phenolic compound and nitrogen-containing heterocyclic compound. The organic sulfur acid-free composition, upon curing at temperatures as low as 130°-140° C., renders void free cured articles having well balanced thermal, chemical and mechanical properties. The organic sulfur acid-free composition may be used in a variety of applications, such as in coatings, structural and non-structural composites and encapsulating systems for electronic and electrical components.

6 Claims, No Drawings

BENZOXAZINE LOW TEMPERATURE CURABLE COMPOSITION

CROSS-REFERENCE TO RELATED APPLICATIONS

This application is the National Phase of International Application PCT/US2016/020800 filed Mar. 4, 2016 which designated the U.S. and which claims priority to U.S. App. Ser. No. 62/127,866 filed Mar. 4, 2015. The noted applications are incorporated herein by reference.

STATEMENT REGARDING FEDERALLY SPONSORED RESEARCH OR DEVELOPMENT

Not applicable.

FIELD OF INVENTION

This disclosure relates to an organic sulfur acid-free composition containing a benzoxazine, a phenolic compound and a nitrogen-containing heterocyclic compound. The organic sulfur acid-free composition exhibits low temperature cure characteristics and is useful in a variety of applications, such as, in an adhesive, sealant, coating, structural and non-structural composites or encapsulating system for electronic and electrical components.

BACKGROUND OF THE INVENTION

Polymers derived from the ring opening polymerization of benzoxazines compete with phenolic, epoxy and other thermoset or thermoplastic resins in various applications, such as in prepregs, laminates, PWB's, molding compounds, sealants, sinter powders, cast articles, structural composites and electrical components. The benzoxazines, which are synthesized by reacting a phenol with an amine and an aldehyde in the presence or absence of a solvent, have been shown to be, upon curing, dimensionally stable with good electrical and mechanical resistance, low shrinkage, low water absorption, and having medium to high glass transition temperatures. One drawback to the use of benzoxazine resins is that they generally require higher curing temperatures in order to build up enough physical properties.

Benzoxazines are known to have been combined with various epoxy resins to produce curable compositions (see e.g., U.S. Pat. No. 4,607,091 (Schreiber), U.S. Pat. No. 5,021,484 (Schreiber), U.S. Pat. No. 5,200,452 (Schreiber) and U.S. Pat. No. 5,443,911 (Schreiber)). Because the epoxy resin reduces the melt viscosity of the benzoxazine, these blends have been shown to be useful in electrical applications since the blend is able to handle higher filler loadings yet still maintain a processable viscosity. One drawback to the use of such blends however is that higher curing temperatures are again usually necessary because of the addition of the epoxy. Furthermore, although these blends exhibit high glass transition temperatures after curing, toughness and stiffness are usually sacrificed to some degree.

More recently, blends of benzoxazines and a dianhydride have been tried (see C. Jubsilpa et al., "Property Enhancement of Polybenzoxazine Modified with Dianhydride", Polymer Degradation and Stability, 96, 1047-1053 (2011)). These blends are solvent-based due to the high melting point and poor processability of the particular dianhydride used, 3,3',4,4'-benzophenonetetracarboxylic dianhydride. These blends are therefore less desirable due to the creation of voids caused by solvent escape, the environmental impact of vaporized solvent, and the redeposition of outgassed molecules on the surface of the cured article.

In U.S. Pat. No. 6,207,786, ternary blends of benzoxazines, epoxy resins, and phenolic resins are disclosed. However, it has been found that the addition of phenolic resins to the blend often lowers crosslink density during curing leading to cured articles having lower than desired glass transition temperatures.

Finally, in U.S. Pat. Pub. 20130266737, a composition containing a polymerization catalyst for curing benzoxazines is disclosed which includes the combination of a nitrogen-containing heterocycle and an organic sulfur-containing acid. However, it is known that use of strong acids in the polymerization of curable materials can negatively affect the physical properties of the cured material.

Notwithstanding the state of the technology, it is an object of the present disclosure to provide an improved benzoxazine-based composition which, upon low temperature cure, is able to perform thermally, mechanically and physically at high temperatures for long periods of time, therefore making it useful in high temperature applications within various industries, such as the aerospace, electronic and automotive industries.

SUMMARY OF THE INVENTION

The present disclosure provides an organic sulfur acid-free composition including a benzoxazine, a phenolic compound and a nitrogen-containing heterocyclic compound. In one embodiment, the organic sulfur acid-free composition, upon curing at a temperature lower than generally used to cure benzoxazine-based systems, for example, about 135° C., provides an article having excellent physical properties, such as, but not limited to, good $T_g$ buildup and excellent flame, smoke and toxicity ("FST") properties.

The organic sulfur acid-free composition according to the present disclosure may be used in a variety of applications such as in a coating, adhesive, sealant, or structural and non-structural composite for use in various industries, such as in the aerospace, automotive or electronic industries.

DETAILED DESCRIPTION OF THE INVENTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. The term "or", unless stated otherwise, refers to the listed members individually as well as in any combination.

The articles "a" and "an" are used herein to refer to one or to more than one (i.e., to at least one) of the grammatical object of the article. By way of example, "a benzoxazine" means one benzoxazine or more than one benzoxazine. The phrases "in one embodiment," "according to one embodiment," and the like generally mean the particular feature, structure, or characteristic following the phrase is included in at least one embodiment of the present invention, and may be included in more than one embodiment of the present disclosure. Importantly, such phases do not necessarily refer to the same embodiment. If the specification states a component or feature "may", "can", "could", or "might" be included or have a characteristic, that particular component or feature is not required to be included or have the characteristic.

As used herein, "hydrocarbyl" means any aliphatic, cycloaliphatic, aromatic, aryl substituted aliphatic or cycloaliphatic, or aliphatic or cycloaliphatic substituted aromatic groups. The aliphatic groups can be saturated or unsaturated.

As used herein, "hydrocarbyloxy" means a hydrocarbyl group having an oxygen linkage between it and the carbon atom to which it is attached Also, as used herein, "organic sulfur acid-free" is intended to mean that no organic sulfur containing acid and/or a derivative of organic sulfur containing acid, such as, but not limited to, organic sulfonic acids and their derivatives, organic sulfuric acids and their derivatives, and mixtures thereof are present in the composition except for trace amounts which may be present as impurities in any of the composition components. In most embodiments, any such impurities are less than 1 mole %, and in other embodiments, less than 0.5 mole %, and in even other embodiments, less than 0.001 mole %, based on the total moles of benzoxazine in the organic sulfur acid-free composition.

According to one embodiment, the organic sulfur acid-free composition contains a benzoxazine. The benzoxazine, which imparts mechanical strength, low water absorption and thermal curability to the composition, may be any curable monomer, oligomer or polymer containing at least one benzoxazine moiety.

Thus, in one embodiment, the benzoxazine may be represented by the general formula

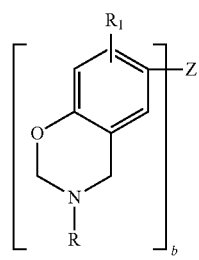
(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and Z is a direct bond (when b=2), a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O. Substituents include, but are not limited to, hydroxy, $C_1$-$C_{20}$ alkyl, a $C_2$-$C_{10}$ alkoxy, mercapto, $C_3$-$C_8$ cycloalkyl, $C_6$-$C_{14}$ heterocyclic, $C_6$-$C_{14}$ aryl, $C_6$-$C_{14}$ heteroaryl, halogen, cyano, nitro, nitrone, amino, amido, acyl, oxyacyl, carboxyl, carbamate, sulfonyl, sulfonamide, and sulfuryl.

In a particular embodiment within formula (1), the benzoxazine may be represented by the following formula:

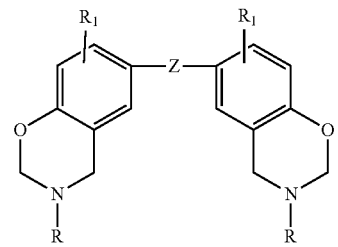
(1a)

where Z is selected from a direct bond, $CH_2$, $C(CH_3)_2$, C=O, O, S, S=O, O=S=O and

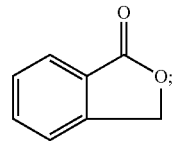

each R is independently hydrogen, a $C_1$-$C_{20}$ alkyl group, an allyl group, or a $C_6$-$C_{14}$ aryl group; and $R_1$ is defined as above.

In another embodiment, the benzoxazine may be embraced by the following general formula

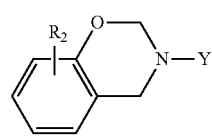
(2)

where Y is a $C_1$-$C_{20}$ alkyl group, a $C_2$-$C_{20}$ alkenyl group, or substituted or unsubstituted phenyl; and $R_2$ is hydrogen, halogen, a $C_1$-$C_{20}$ alkyl group, or a $C_2$-$C_{20}$ alkenyl group. Suitable substituents for phenyl are as set forth above.

In a particular embodiment within formula (2), the benzoxazine may be represented by the following formula

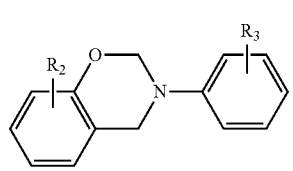
(2a)

where $R_2$ is a $C_1$-$C_{20}$ alkyl or $C_2$-$C_{20}$ alkenyl group, each of which is optionally substituted or interrupted by one or more O, N, S, C=O, COO and NHC=O, and a $C_6$-$C_{20}$ aryl group; and $R_3$ is hydrogen, a $C_1$-$C_{20}$ alkyl or $C_2$-$C_{20}$ alkenyl group, each of which is optionally substituted or interrupted by one or more O, N, S, C=O, COOH and NHC=O or a $C_6$-$C_{20}$ aryl group.

Alternatively, the benzoxazine may be embraced by the following general formula

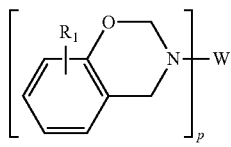
(3)

where p is 2, W is selected from biphenyl, diphenyl methane, diphenyl isopropane, diphenyl sulfide, diphenyl sulfoxide, diphenyl sulfone, and diphenyl ketone, and $R_1$ is defined as above.

In the present disclosure, combinations of multifunctional benzoxazines and monofunctional benzoxazines, or combinations of one or more multifunctional benzoxazines and one or more monofunctional benzoxazines may be used.

The benzoxazines are commercially available from several sources including Huntsman Advanced Materials Americas LLC, Georgia Pacific Resins Inc. and Shikoku Chemicals Corporation.

The benzoxazines may also be obtained by reacting a phenol, for example, bisphenol A, bisphenol F or phenolphthalein, with an aldehyde, for example, formaldehyde, and a primary amine, under conditions in which water is removed. The molar ratio of phenol to aldehyde reactant may be from about 1:3 to 1:10, alternatively from about 1:4 to 1:7. In still another embodiment, the molar ratio of phenol to aldehyde reactant may be from about 1:4.5 to 1:5. The molar ratio of phenol to primary amine reactant may be from about 1:1 to 1:3, alternatively from about 1:1.4 to 1:2.5. In still another embodiment, the molar ratio of phenol to primary amine reactant may be from about 1:2.1 to 1:2.2.

Examples of primary amines include: aromatic mono- or di-amines, aliphatic amines, cycloaliphatic amines and heterocyclic monoamines; for example, aniline, o-, m- and p-phenylene diamine, benzidine, 4,4'-diaminodiphenyl methane, cyclohexylamine, butylamine, methylamine, hexylamine, allylamine, furfurylamine ethylenediamine, and propylenediamine. The amines may, in their respective carbon part, be substituted by $C_1$-$C_8$ alkyl or allyl. In one embodiment, the primary amine is a compound having the general formula $R_aNH_2$, wherein $R_a$ is allyl, unsubstituted or substituted phenyl, unsubstituted or substituted $C_1$-$C_8$ alkyl or unsubstituted or substituted $C_3$-$C_8$ cycloalkyl. Suitable substituents on the $R_a$ group include, but are not limited to, amino, $C_1$-$C_4$ alkyl and allyl. In some embodiments, one to four substituents may be present on the $R_a$ group. In one particular embodiment, $R_a$ is phenyl.

According to one embodiment, the benzoxazine may be included in the organic sulfur acid-free composition in an amount in the range of between about 10% to about 98% by weight, based on the total weight of the organic sulfur acid-free composition. In another embodiment, the benzoxazine may be included in the organic sulfur acid-free composition in an amount in the range of between about 25% to about 95% by weight, based on the total weight of the organic sulfur acid-free composition. In still another embodiment, the benzoxazine may be included in the organic sulfur acid-free composition in an amount in the range of between about 30% by weight to about 90% by weight, based on the total weight of the organic sulfur acid-free composition.

According to one embodiment, the organic sulfur acid-free composition also contains a phenolic compound. The phenolic compound may be a monofunctional phenolic compound, a difunctional phenolic compound, a multifunctional phenolic compound or mixtures thereof.

In one embodiment, the phenolic compound is a monofunctional compound having the formula (4)

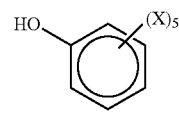
(4)

where each X is independently hydrogen, halogen, a hydrocarbyl group having from 1 to 20 carbon atoms or a hydrocarbyloxy group having from 1 to 20 carbon atoms. Examples of monofunctional phenolic compounds include, but are not limited to, phenol, cresol, t-butyl phenol, chlorophenol, 2, 4, 6-trichlorophenol, dimethylphenol, 2,6-dimethylphenol, 2-bromo-4-methylphenol and trimethylphenol.

According to another embodiment, the phenolic compound is a difunctional phenolic compound. The difunctional phenolic compound may be a dinuclear diphenol ("bisphenol") or mononuclear diphenol ("diphenol'). In one embodiment, the difunctional phenolic compound is a compound having the formula (5)

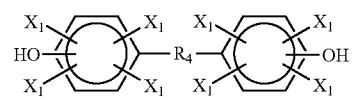
(5)

where each $X_1$ is independently hydrogen, a $C_1$-$C_{20}$ alkyl group, an alkoxy group, an alloxy group or a halogen; and $R_4$ is a direct bond, a $C_1$-$C_{20}$ alkyl group,

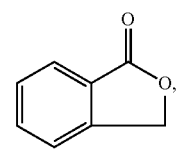

—O—, —S—, —S—S—, —S(=O)—, —(O=)S(=O)—, —C(=O)—, —C(=O)—O—, —OC(O)—O—, —(O=)C—C(=O)—, —NHC(=O)— or —NHC(=O)—O—.

Examples of compounds of formula (5) include, but are not limited to, bisphenol A, bisphenol F, bisphenol E, bisphenol Z, bisphenol AP, bisphenol S, tetramethylbisphenol A, tetramethylbisphenol F, tetra-t-butylbisphenol A, 4,4'-methylenebis(2,6-di-t-butylphenol), 2,2'-methylenebis(4,6-di-t-butylphenol), tetramethylbisphenol S, tetrabromobisphenol A, tetrabromobisphenol F, biphenol, tetramethylbiphenol, tetra-t-butylbiphenol, bisphenol C, 4,4'-ethylenebis(3-methyl-6-t-butylphenol), dihydroxydiphenyl ether, dihydroxydiphenyl thioether, dihydroxybenzophenone, tetrabromobisphenol S, 2,2'-isobutylidenebis(4,6-dimethylphenol), bisphenol AF, bis-hydroxyphenyl) fluorene, 1,3-bis(hydroxycumyl)benzene, 1,4-bis (hydroxycumyl)benzene, diphenylbis(4-hydroxyphenyl) methane, 1,4-bis(3,5-dimethyl-4-hydroxycumyl)benzene, 4,4'-butylidenebis (6-t-butyl-3-methylphenol), tetramethylbisphenol Z, 4,4-[1,3phenylenebis(1-methyl ethylidene)]bis[2,6-dimethyl]phenol, 4,4'-[1,3-phenylenebis-(1-methylethylidene)]bis[2-t-butyl-5-methyl]phenol, phenolphthalein, and 4,4'-[1,3-phenylenebis-(1-methylthylidene)]bis (2-cyclohexyl-5-methylphenol).

Other examples of the difunctional phenolic compound represented by the formula (5) are various compounds other than the above-mentioned compounds, wherein in the general formula (5), $R_4$ is methylene, ethylidene, α-methylbenzylidene, cyclohexylidene, isopropylidene, butylidene, p-xylene-α,α'-diyl, or fluorene-9-ylidene, or $R_4$ is a divalent hydrocarbon group formed when adding phenols to dicyclopentadiene or a cyclic terpene compound (e.g., limonene, terpinolene, pinene, terpinene or menthadiene).

In another embodiment, the difunctional phenolic compound is a compound having the formula (6)

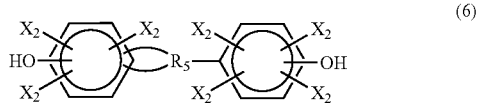

(6)

where each $X_2$ is independently represents hydrogen, a $C_1$-$C_{20}$ alkyl group, an alkoxy group, an alloxy group or halogen; and $R_5$ represents a trivalent hydrocarbon group having 1 to 20 carbon atoms or a trivalent hydrocarbon group containing an intermediate ether bond and having 2 to 20 total carbon atoms.

An example of a compound of formula (6) includes

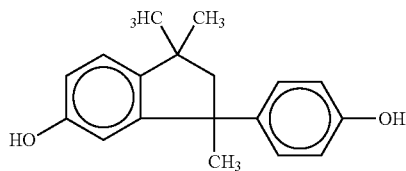

In another embodiment, the difunctional phenolic compound is a compound having the formula (7)

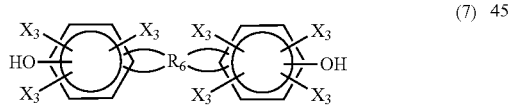

(7)

where each $X_3$ is independently hydrogen, a $C_1$-$C_{20}$ alkyl group, an alkoxy group, an alloxy group or halogen, and $R_6$ represents a tetravalent hydrocarbon group having 1 to 20 carbon atoms, or a tetravalent hydrocarbon group containing an intermediate ether bond and having 2 to 20 total carbon atoms.

Examples of compounds having the formula (7) include

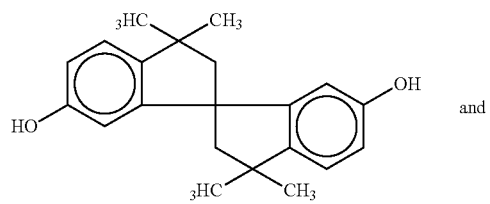

and

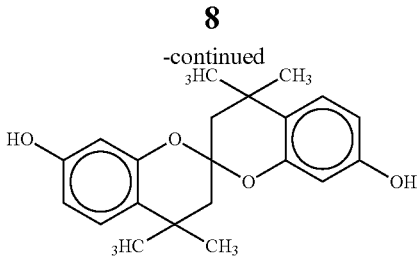

In still another embodiment, the difunctional phenolic compound is a compound having the formula (8)

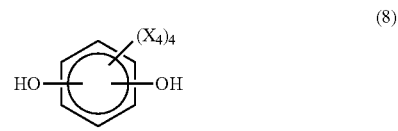

(8)

where each $X_4$ is independently hydrogen, a $C_1$-$C_{20}$ alkyl group, an alkoxy group, an alloxy group or halogen.

Examples of compounds of the formula (8) include, but are not limited to, hydroquinone, resorcinol, catechol, methylhydroquinone, 2,5-dimethylhydroquinone, 2-6-dimethylhydroquinone, trimethylhydroquinone, tetramethylhydroquinone, t-butylhydroquinone, 2,5-di-t-butylhydroquinone, 2-ethyl-5-methylhydroquinone, isopropylhydroquinone, 2-methylresorcinol, 5-methylresorcinol, 4-bromoresorcinol, 5-methoxyresorcinol, 2,4,6-trimethylresorcinol, 4-cumylresorcinol, 2,5diproylhydroquinone, 2-propyl-3,5,6-trimethylhydroquinone, cumylhydroquinone and 2,5-di-t-hexylhydroquinone.

In yet another embodiment, the difunctional phenolic compound is a compound of the formula (9)

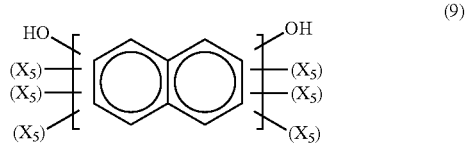

(9)

where each $X_5$ is independently hydrogen, a $C_1$-$C_{20}$ alkyl group, an alkoxy group, an alloxy group or halogen.

Examples of compounds of the formula (9) include, but are not limited to, 1,2-dihydroxynaphthalene, 1,3-dihydroxynaphthalene, 1,4-dihydroxy naphthalene, 1,5-dihydroxynaphthalene, 1,6-dihydroxynaphthalene, 1,7-dihydroxynaphthalene, 2,3-dihydroxynaphthalene, 2,6-dihydroxynaphthalene, 2,7-dihydroxynaphthalene, 1,5-dihydroxy-7-methylnaphthalene, 1,6 dihydroxy-2-methylnaphthalene, 1,6-dihydroxy-8-methylnaphthalene, 1,6-dihydroxy-4,8-dimethylnaphthalene, 2-bromo-1,6-dihydroxy naphthalene and 8-bromo-1,6-dihydroxynaphthalene.

In still another embodiment, the phenolic compound is a multifunctional phenolic compound having at least 3 hydroxyl groups. Examples of such compounds include pyrogallol (also known as 1,2,3-trihydroxybenzol), or 1,2,4-trihydroxybenzol (also known as hydroxyhydrochinon), 1,8,9-trihydroxyanthracene (also known as dithranol or 1,8,9-anthracentriol), or 1,2, 10-trihydroxyanthracene (also known as anthrarobine), 2,4,5-trihydroxypyrimidine, tris(hydroxyphenyl)methane and tetraphenolethane. Further examples include phenolic resins obtained from phenols, cresols, xylenols or alkyl phenols and formaldehyde, such as phenol novolac resins, cresol novolac resins or resole resins (for e.g. phenol-formaldehyde resole, cresol-formaldehyde resole, phenol formaldehyde resole, bisphenol F-formaldehyde resole, and bisphenol A-formaldehyde resole) as described in Lee & Neville, section 11-14, 3,4,5-trihydroxybenzoic acid (also known as gallic acid) or its derivatives, 2,4,5-trihydroxypyrimidine, dicyclopentadiene phenol novolac, and copolymers of styrene and hydroxystyrene. Some of these compounds have the formulae

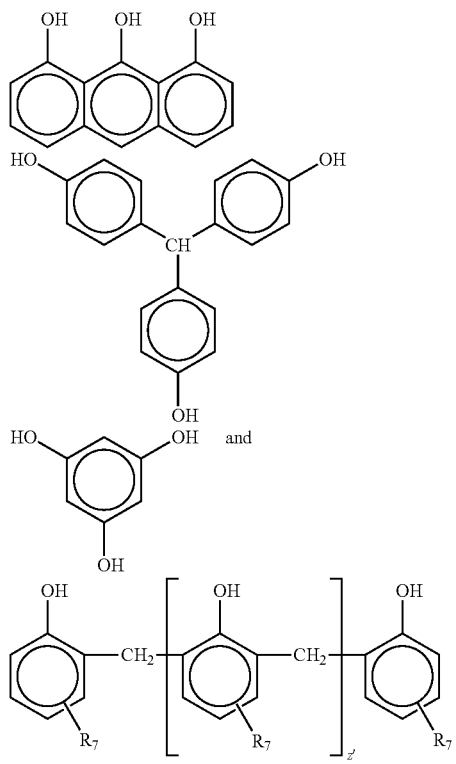

where $R_7$ is hydrogen or a $C_1$-$C_3$ alkyl group and z' is an integer from 1 to 10.

Phenolic compounds for use herein are commercially available from several sources, including, but not limited to, Momentive Specialty Chemicals, Georgia-Pacific and Durez Corporation.

According to one embodiment, the phenolic compound may be included in the organic sulfur acid-free composition in an amount in the range of between about 2% by weight to about 70% by weight, based on the total weight of the organic sulfur acid-free composition. In another embodiment, the phenolic compound may be included in the organic sulfur acid-free composition in an amount in the range of greater than 3% by weight to about 60% by weight, based on the total weight of the organic sulfur acid-free composition. In yet another embodiment, the phenolic compound may be included in the organic sulfur acid-free composition in an amount in the range of between about 5% by weight to about 40% by weight, based on the total weight of the organic sulfur acid-free composition.

According to a further embodiment, the organic sulfur acid-free composition also contains a nitrogen-containing heterocyclic compound. The nitrogen-containing heterocyclic compound may be an imidazole, imidazolidine, imidazoline, oxazole, pyrrole, thiazole, pyridine, pyrazine, morpholine, pyridazine, pyrimidine, pyrrolidine, pyrazole, phthalazine, quinoline, purine, indazole, indole, indolizine, pyrroline, indoline, piperidine, piperazine or combinations thereof.

In one embodiment, the nitrogen-containing heterocyclic compound is an imidazole having the formula (10)

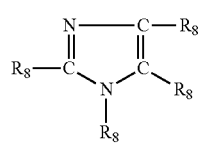

(10)

where each $R_8$ is independently hydrogen, halogen, cyano, a hydrocarbyl group having from 1 to about 18 carbon atoms, a hydrocarbyloxy group having from 1 to 18 carbon atoms, or two of the $R_8$'s can combine to form a 5 or 6 membered ring with the carbon and nitrogen atoms from the imidazole ring to which they are attached or two of the $R_8$'s can combine to form a 5 or 6 membered ring with the two carbon atoms from the imidazole ring to which they are attached.

Examples of imidazole's of the formula (10) include, for example, imidazole, 2-methylimidazole, 2-ethylimidazole, 2-propylimidazole, 2-butylimidazole, 2-pentylimidazole, 2-hexylimidazole, 2-cyclohexylimidazole, 2-phenylimidazole, 2-nonylimidazole, 2-undecylimidazole, 2-heptadecylimidazole, 2-ethyl-4-methylimidazole, 2-phenyl-4-methylimidazole, 1-benzylimidazole, 1-ethyl-2-methylbenzimidazole, 2-methyl-5,6-benzimidazole, 1-vinylimidazole, 1-allyl-2-methylimidazole, 2-cyanoimidazole, 2-chloroimidazole, 2-bromoimidazole, 1-(2-hydroxypropyl)-2-methylimidazole, 2-phenyl-4,5-dimethylolimidazole, 2-phenyl-4-methyl-5-hydroxymethylimidazole and 2-hydroxybenzimidazole.

In a further embodiment, the nitrogen-containing heterocyclic compound is selected from 2-methylimidazole, 2-ethyl-4-methylimidazole, 1,2-dimethylimidazole and 2-phenylimidazole.

According to another embodiment, the nitrogen-containing heterocyclic compound is a pyrazole having the formula (11)

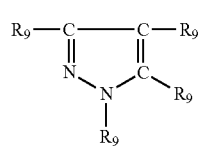

(11)

where each $R_9$ is independently hydrogen, halogen, cyano, a hydrocarbyl group having from 1 to about 18 carbon atoms, a hydrocarbyloxy group having from 1 to 18 carbon atoms, or two of the $R_9$'s can combine to form a 5 or 6 membered ring with the carbon and nitrogen atoms from the pyrazole ring to which they are attached or two of the $R_9$'s can combine to form a 5 or 6 membered ring with the two carbon atoms from the pyrazole ring to which they are attached.

Examples of pyrazole's of formula (11) include, but are not limited to, pyrazole, 1-methylpyrazole, 3-methylpyrazole, 4-butylpyrazole, 1-methyl-3-propylpyrazole, 3-ethyl-5-methylpyrazole, 1-(3-hydroxypropyl)pyrazole, 5-phenylpyrazole, 5-benzylpyrazole, 1-phenyl-3-methylpyrazole, 1-cyanopyrazole, 3-chloropyrazole and 4-bromo-1-methylpyrazole.

In another embodiment, the nitrogen-containing heterocyclic compound is an oxazole having the formula (12)

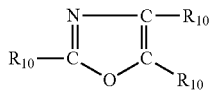
(12)

where each $R_{10}$ is independently hydrogen, halogen, cyano or a hydrocarbyl group having from 1 to about 18 carbon atoms or a hydrocarbyloxy group having from 1 to 18 carbon atoms.

Examples of oxazole's of the formula (12) include oxazole, 4-methyloxazole, 2-methyloxazole, 4-butyloxazole, 2-methyl-5-propyloxazole, 2-ethyl-4-methyloxazole, 2-(3-hydroxypropyl)oxazole, 4-phenyloxazole, 5-benzyloxazole, 2-phenyl-5-methyloxazole, 2-cyanooxazole, 4-chlorooxazole and 4-bromo-2-methyloxazole.

According to another embodiment, the nitrogen-containing heterocyclic compound is an imidazolidine having the formula (13)

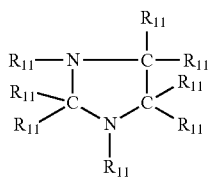
(13)

where each $R_{11}$ is independently hydrogen, halogen, cyano, a hydrocarbyl group having from 1 to about 18 carbon atoms or a hydrocarbyloxy group having from 1 to 18 carbon atoms.

Examples of imidazolidine's of formula (13) include, but are not limited to imidazolidine, 1-methylimidazolidine, 2-methylimidazolidine, 4-butylimidazolidine, 1-methyl-3-propylimidazolidine, 1-ethyl-4-methylimidazolidine, 1-(3-hydroxypropyl)imidazolidine, 2-phenylimidazolidine, 1-benzylimidazolidine, 2-phenyl-1-methylimidazolidine, 4-cyanoimidazolidine, 4-chloroimidazolidine and 4-bromo-1-methylimidazolidine.

In another embodiment, the nitrogen-containing compound is an imidazoline having the formula (14)

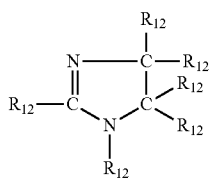
(14)

where each $R_{12}$ is independently hydrogen, halogen, cyano, a hydrocarbyl group having from 1 to about 18 carbon atoms or a hydrocarbyloxy group having from 1 to 18 carbon atoms.

Examples of imidazoline's of formula (14) include, but are not limited to, imidazoline, 1-methylimidazolidine, 2-methylimidazolidine, 4-butylimidazolidine, 1-methyl-2-propylimidazolidine, 1-ethyl-4-methylimidazolidine, 1-(3-hydroxypropyl)imidazolidine, 2-phenylimidazolidine, 1-benzylimidazolidine, 2-phenyl-1-methylimidazolidine, 4-cyanoimidazolidine, 5-chloroimidazolidine and 5-bromo-1-methylimidazolidine.

In yet another embodiment, the nitrogen-containing heterocyclic compound is a thiazole having the formula (15)

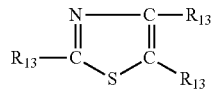
(15)

where each $R_{13}$ is independently hydrogen, halogen, cyano, a hydrocarbyl group having from 1 to about 18 carbon atoms or a hydrocarbyloxy group having from 1 to 18 carbon atoms.

Examples of thiazole's of formula (15) include, but are not limited to, thiazole, 2-methylthiazole, 5-methylthiazole, 4-butylthiazole, 2-methyl-4-propylthiazole, 4-ethyl-5-methylthiazole, 2-(3-hydroxypropyl)thiazole, 2-phenylthiazole, 2-benzylthiazole, 4-phenyl-5-methylthiazole, 2-cyanothiazole, 5-chlorothiazole and 5-bromo-2-methylthiazole.

In another embodiment, the nitrogen-containing heterocyclic compound is a pyrrole having the formula (16)

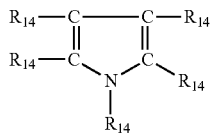
(16)

where each $R_{14}$ is independently hydrogen, halogen, cyano, a hydrocarbyl group having from 1 to about 18 carbon atoms or a hydrocarbyloxy group having from 1 to 18 carbon atoms.

Examples of pyrrole's of formula (16) include, but are not limited to, pyrrole, 1-methylpyrrole, 2-methylpyrrole, 3-butylpyrrole, 1-methyl-2-propylpyrrole, 2-ethyl-3-methylpyrrole, 1-(3-hydroxypropyl)pyrrole, 2-phenylpyrrole, 1-benzylpyrrole, 2-phenyl-1-methylpyrrole, 3-cyanopyrrole, 3-chloropyrrole and 2-bromo-1-methylpyrrole.

In a further embodiment, the nitrogen-containing heterocyclic compound is a pyrazine having the formula (17)

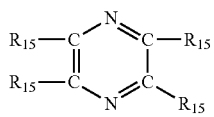
(17)

where each $R_{15}$ is independently hydrogen, halogen, cyano, a hydrocarbyl group having from 1 to about 18 carbon atoms or a hydrocarbyloxy group having from 1 to 18 carbon atoms.

Examples of pyrazines of formula (17) include, but are not limited to, pyrazine, 2-methylpyrazine, 3-methylpyrazine, 2-butylpyrazine, 2-methyl-5-propylpyrazine, 2-ethyl-6-methylpyrazine, 2-(3-hydroxypropyl)pyrazine, 2-phenylpyrazine, 2-benzylpyrazine, 2-phenyl-3-methylpyrazine, 2-cyanopyrazine, 2-chloropyrazine and 2-bromo-5-methylpyrazine.

In still another embodiment, the nitrogen-containing heterocyclic compound is a pyridine having the formula (18)

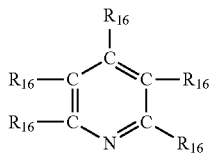

(18)

where each $R_{16}$ is independently hydrogen, halogen, cyano, a hydrocarbyl group having from 1 to about 18 carbon atoms or a hydrocarbyloxy group having from 1 to 18 carbon atoms.

Examples of pyridines of formula (18) include, but are not limited to, pyridine, 2-methylpyridine, 3-methylpyridine, 4-butylpyridine, 2-methyl-3-propylpyridine, 3-ethyl-4-methylpyridine, 4-(3-hydroxypropyl)pyridine, 2-phenylpyridine, 3-benzylpyridine, 4-phenyl-2-methylpyridine, 3-cyanopyridine, 2-chloropyridine and 3-bromo-5-methylpyridine.

In another embodiment, the nitrogen-containing heterocyclic compound is a pyridazine having the formula (19)

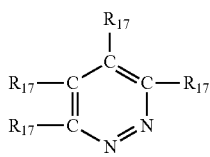

(19)

where each $R_{17}$ is independently hydrogen, halogen, cyano, a hydrocarbyl group having from 1 to about 18 carbon atoms or a hydrocarbyloxy group having from 1 to 18 carbon atoms.

Examples of pyridazine's of formula (19) include, but are not limited to pyridazine, 3-methylpyridazine, 4-methylpyridazine, 3-butylpyridazine, 3-methyl-4-propylpyridazine, 3-ethyl-6-methylpyridazine, 4-(3-hydroxypropyl)pyridazine, 3-phenylpyridazine, 4-benzylpyridazine, 4-phenyl-5-methylpyridazine, 4-cyanopyridazine, 4-chloropyridazine and 3-bromo-5-methylpyridazine.

According to another embodiment, the nitrogen-containing heterocyclic compound is a pyrrolidine having the formula (20)

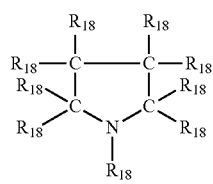

(20)

where each $R_{18}$ is independently hydrogen, halogen, cyano, a hydrocarbyl group having from 1 to about 18 carbon atoms or a hydrocarbyloxy group having from 1 to 18 carbon atoms.

Examples of pyrrolidine's of formula (20) include, but are not limited to, pyrrolidine, 1-methyl-pyrrolidine, 4-phenylpyrrolidine, 2-methylpyrrolidine, 3-methylpyrrolidine, 1-butylpyrrolidine, 1-methyl-2-propylpyrrolidine, 3-ethyl-4-methyl-pyrrolidine, 2-(3-hydroxypropyl)pyrrolidine, 1-phenyl-2-methylpyrrolidine, 2-cyanopyrrolidine, 2-chloropyrrolidine and 2-bromo-1-methylpyrrolidine.

In another embodiment, the nitrogen-containing heterocyclic compound is a morpholine having the formula (21)

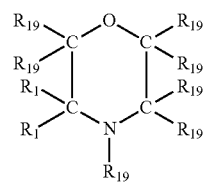

(21)

where each $R_{19}$ is independently hydrogen, halogen, cyano, a hydrocarbyl group having from 1 to about 18 carbon atoms or a hydrocarbyloxy group having from 1 to 18 carbon atoms.

Examples of morpholine's of formula (21) include, but are not limited to, morpholine, 4-methylmorpholine, 3-methylmorpholine, 4-butylmorpholine, 4-methyl-3-propylmorpholine, 2-ethyl-3-methylmorpholine, 4-(3-hydroxypropyl)morpholine, 2-phenylmorpholine, 4-benzylmorpholine, 3-phenyl-1-methylmorpholine, 3-cyanomorpholine, 3-chloromorpholine and 3-bromo-4-methylmorpholine.

In another embodiment, the nitrogen-containing heterocyclic compound is a pyrimidine having the formula (22)

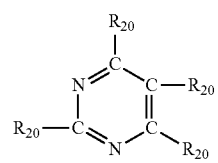

(22)

where each $R_{20}$ is independently hydrogen, halogen, cyano, a hydrocarbyl group having from 1 to about 18 carbon atoms or a hydrocarbyloxy group having from 1 to 18 carbon atoms.

Examples of pyrimidines of formula (22) include, but are not limited to, pyrimidine, 2-methylpyrimidine, 4-methylpyrimidine, 2-butylpyrimidine, 2-methyl-4-propylpyrimidine, 4-ethyl-5-methylpyrimidine, 2-(3-hydroxypropyl)pyrimidine, 2-phenylpyrimidine, 2-benzylpyrimidine, 4-phenyl-2-methylpyrimidine, 4-cyanopyrimidine, 2-chloropyrimidine and 4-bromo-2-methylpyrimidine.

In still another embodiment, the nitrogen-containing heterocyclic compound is an indolizine having the formula (23)

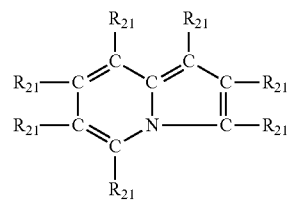

(23)

where each $R_{21}$ is independently hydrogen, halogen, cyano, a hydrocarbyl group having from 1 to about 18 carbon atoms or a hydrocarbyloxy group having from 1 to 18 carbon atoms.

Examples of indolizine's of formula (23) include, but are not limited to, indolizine, 1-methylindolizine, 2-methylindolizine, 3-butylindolizine, 5-methyl-1-propylindolizine, 2-ethyl-1-methylindolizine, 6-(3-hydroxypropyl)indolizine, 3-phenylindolizine, 7-benzylindolizine, 2-phenyl-3-methylindolizine, 5-cyanoindolizine, 7-chloroindolizine and 3-bromo-5-methylindolizine.

In another embodiment, the nitrogen-containing heterocyclic compound is a pyrroline having the formula (24)

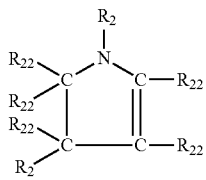

(24)

where each $R_{22}$ is independently hydrogen, halogen, cyano, a hydrocarbyl group having from 1 to about 18 carbon atoms or a hydrocarbyloxy group having from 1 to 18 carbon atoms.

Examples of pyrroline's of formula (24) include, but are not limited to, pyrroline, 2-methylpyrroline, 4-methyl-pyrroline, 5-butylpyrroline, 5-methyl-1-propyl-pyrroline, 1-ethyl-3-methylpyrroline, 1-(3-hydroxy-propyl)pyrroline, 5-phenylpyrroline, 1-benzylpyrroline, 1-phenyl-4-methylpyrroline, 3-cyanopyrroline, 5-chloropyrroline and 2-bromo-1-methylpyrroline.

In another embodiment, the nitrogen-containing heterocyclic compound is an indoline having the formula (25)

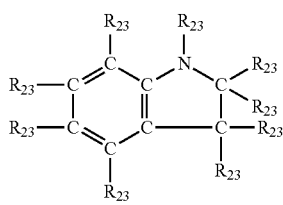

(25)

where each $R_{23}$ is independently hydrogen, halogen, cyano, a hydrocarbyl group having from 1 to about 18 carbon atoms or a hydrocarbyloxy group having from 1 to 18 carbon atoms.

Examples of indoline's of formula (25) include, but are not limited to, indoline, 1-methylindoline, 2-methylindoline, 3-butylindoline, 1-methyl-2-propyl-indoline, 2-ethyl-2-methylindoline, 1-(3-hydroxy-propyl)indoline, 1-phenylindoline, 1-benzylindoline, 1-phenyl-2-methylindoline, 1-benzylindoline, 1-phenyl-2-methylindoline, 5-cyanoindoline, 7-chloroindoline and 5-bromo-1-methylindoline.

In a further embodiment, the nitrogen-containing heterocyclic compound is a piperidine having the formula (26)

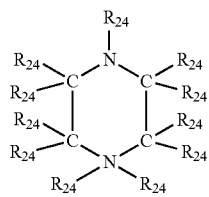

(26)

where each $R_{24}$ is independently hydrogen, halogen, cyano, a hydrocarbyl group having from 1 to about 18 carbon atoms or a hydrocarbyloxy group having from 1 to 18 carbon atoms.

Examples of piperidine's of formula (26) include, but are not limited to, piperidine, 1-methylpiperidine, 2-methylpiperidine, 3-butylpiperidine, 1-methyl-2-propypiperidine, 2-ethyl-4-methylpiperidine, 1-(3-hydroxypropyl)piperdine, 1-phenylpiperidine, 1-benzylpiperidine, 1-phenyl-2-methylpiperidine, 4-cyanopiperdine, 3-chloropiperidine and 4-bromo-1-methylpiperidine.

In another embodiment, the nitrogen-containing heterocyclic compound is a piperazine having the formula (27)

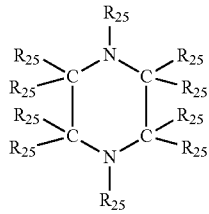

(27)

where each $R_{25}$ is independently hydrogen, halogen, cyano, a hydrocarbyl group having from 1 to about 18 carbon atoms or a hydrocarbyloxy group having from 1 to 18 carbon atoms.

Examples of piperazine's of formula (27) include, but are not limited to, piperazine, 1-methylpiperazine, 2-methylpiperazine, 3-butylpiperazine, 1-methyl-4-propylpiperazine, 1-ethyl-3-methylpiperazine, 1(3-hydroxypropyl)-piperazine, 2-phenylpiperazine, 1-benzylpiperazine, 1-methyl-3-phenylpiperazine, 2-cyanopiperazine, 2-chloropiperazine and 1,4-dimethyl-2-bromopiperazine.

In another embodiment, the nitrogen-containing heterocyclic compound is a phthalazine having the formula (28)

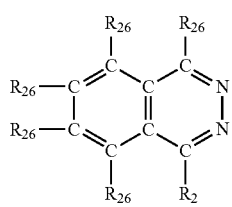

(28)

where each $R_{26}$ is independently hydrogen, halogen, cyano, a hydrocarbyl group having from 1 to about 18 carbon atoms or a hydrocarbyloxy group having from 1 to 18 carbon atoms.

Examples of phthalazine's of formula (28) include, but are not limited to, phthalazine, 1-methylphthalazine, 6-methylphthalazine, 1-butylphthalazine, 1-methyl-4-propylphthalazine, 1-ethyl-6-methylphthalazine, 1-(3-hydroxypropyl)phthalazine, 5-phenylphthalazine, 1-benzylphthalazine, 1-phenyl-4-methylphthalazine, 1-cyanophthalazine, 1-chlorophthalazine and 1-bromo-4-methylphthalazine.

In another embodiment, the nitrogen-containing heterocyclic compound is a quinoline having the formula (29)

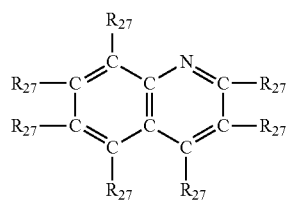

(29)

where each $R_{27}$ is independently hydrogen, halogen, cyano, a hydrocarbyl group having from 1 to about 18 carbon atoms or a hydrocarbyloxy group having from 1 to 18 carbon atoms.

Examples of quinoline's of formula (29) include, but are not limited to, quinoline, 2-methylquinoline, 3-methylquinoline, 4-butylquinoline, 5-methyl-2-propylquinoline, 2-ethyl-3-methylquinoline, 3-(3-hydroxypropyl)quinoline, 3-phenylquinoline, 4-benzylquinoline, 3-phenyl-2-methylquinoline, 3-cyanoquinoline, 4-chloroquinoline and 2-bromo-3-methylquinoline.

In another embodiment, the nitrogen-containing heterocyclic compound is a purine having the formula (30)

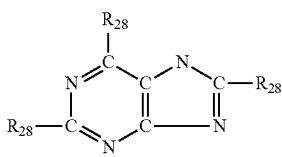

(30)

where each $R_{28}$ is independently hydrogen, halogen, cyano, a hydrocarbyl group having from 1 to about 18 carbon atoms or a hydrocarbyloxy group having from 1 to 18 carbon atoms.

Examples of purines of formula (30) include, but are not limited to, purine, 2-methylpurine, 8-methylpurine, 6-butylpurine, 2-methyl-8-propylpurine, 6-ethyl-8-methylpurine, 8-(3-hydroxypropyl)purine, 2-phenylpurine, 2-benzylpurine, 6-phenyl-2-methylpurine, 8-cyanopurine, 2-chloropurine and 8-bromo-2-methylpurine.

In a further embodiment, the nitrogen-containing heterocyclic compound is an indazole having the formula (31)

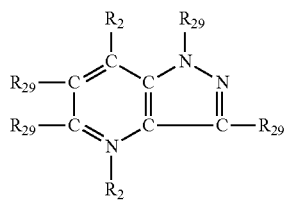

(31)

where each $R_{29}$ is independently hydrogen, halogen, cyano, a hydrocarbyl group having from 1 to about 18 carbon atoms or a hydrocarbyloxy group having from 1 to 18 carbon atoms.

Examples of indazole's of formula (31) include, but are not limited to, indazole, 1-methylindazole, 3-methylindazole, 1-butylindazole, 1-methyl-3-propylindazole, 1-ethyl-5-methylindazole, 3-(3-hydroxypropyl)indazole, 3-phenylindazole, 6-benzylindazole, 6-phenyl-1-methylindazole, 3-cyanoindazole, 5-chloroindazole and 3-bromo-1-methylindazole.

In a further embodiment, the nitrogen-containing heterocyclic compound is an indole having the formula (32)

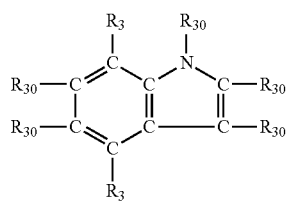

(32)

where each $R_{30}$ is independently hydrogen, halogen, cyano, a hydrocarbyl group having from 1 to about 18 carbon atoms or a hydrocarbyloxy group having from 1 to 18 carbon atoms.

Examples of indoles of formula (32) include, but are not limited to, indole, 1-methylindole, 2-methylindole, 3-butylindole, 1-methyl-2-propylindole, 2-ethyl-3-methylindole, 1-(3-hydroxypropyl)indole, 2-phenylindole, 1-benzylindole, 2-phenyl-1-methylindole, 2-cyanoindole, 5-chloroindole and 3-bromo-1-methylindole.

According to one embodiment, the nitrogen-containing heterocyclic compound may be included in the organic sulfur acid-free composition in an amount in the range of between about 0.01% by weight to about 30% by weight, based on the total weight of the organic sulfur acid-free composition. In another embodiment, the nitrogen-containing heterocyclic compound may be included in the organic sulfur acid-free composition in an amount in the range of about 0.05% by weight to about 22.5% by weight, based on the total weight of the organic sulfur acid-free composition. In yet another embodiment, the nitrogen-containing heterocyclic compound may be included in the organic sulfur acid-free composition in an amount in the range of about 0.1% by weight to about 15% by weight, while in still other embodiments in an amount in the range between about 0.5% by weight to about 3% by weight, based on the total weight of the organic sulfur acid-free composition.

In some embodiments, the organic sulfur acid-free composition may optionally contain a solvent. Examples of solvents that may be included are methylethylketone, acetone, N-methyl-2-pyrrolidone, N,N-dimethyl formamide, pentanol, butanol, dioxolane, isopropanol, methoxy propanol, methoxy propanol acetate, dimethylformamide, glycols, glycol acetates and toluene, xylene. The ketones and the glycols are especially preferred. Typically, the organic sulfur acid-free composition may contain about 20% by weight to about 30% by weight of solvent, based on the total weight of the organic sulfur acid-free composition.

The organic sulfur acid-free composition may also optionally include one or more additives. Examples of such additives, include, but are not limited to, a flame retardant, a toughener, catalyst, reinforcing agent, filler and mixtures thereof.

Examples of flame retardants include, but are not limited to, phosphorous flame retardants, such as DOPO (9,10-dihydro-9-oxa-phosphaphenanthrene-10-oxide), fyroflex PMP (Akzo; a reactive organophosphorus additive modified with hydroxyl groups at its chain ends and able to react with epoxy resins), CN2645A (Great Lakes; a material which is based on phosphine oxide chemistry and contains phenolic functionality able to react with epoxy resins), and OP 930 (Clariant), brominated polyphenylene oxid and ferrocene.

Examples of tougheners which may be used include copolymers based on butadiene/acrylonitrile, butadiene/(meth)acrylic acid esters, butadiene/acrylonitrile/styrene graft copolymers ("ABS"), butadiene/methyl methacrylate/styrene graft copolymers ("MBS"), poly(propylene) oxides, amine-terminated butadiene/acrylonitrile copolymers ("ATBN") and hydroxyl-terminated polyether sulfones, such as PES 5003P, available commercially from Sumitomo Chemical Company or RADEL® polymer from Solvay Advanced Polymers, LLC, core shell rubber and polymers, such as PS 1700, available commercially from Union Carbide Corporation, rubber particles having a core-shell structure in an epoxy resin matrix such as MX-120 resin from Kaneka Corporation, Genioperal M23A resin from Wacker Chemie GmbH, rubber-modified epoxy resin, for instance an epoxy-terminated adduct of an epoxy resin and a diene rubber or a conjugated diene/nitrile rubber.

Examples of catalysts which may be used include amines and polyaminoamides.

Examples of filler and reinforcing agents which may be used include silica, silica nanoparticles pre-dispersed in epoxy resins, coal tar, bitumen, textile fibres, glass fibres, asbestos fibres, boron fibres, carbon fibres, mineral silicates, mica, powdered quartz, hydrated aluminum oxide, bentonite, wollastonite, kaolin, aerogel or metal powders, for example aluminum powder or iron powder, and also pigments and dyes, such as carbon black, oxide colors and titanium dioxide, light weight microballoons, such as cenospheres, glass microspheres, carbon and polymer microballoons, thixotropic agents, flow control agents, such as silicones, waxes and stearates, which can, in part, also be used as mold release agents, adhesion promoters, antioxidants and light stabilizers, the particle size and distribution many of which may be controlled to vary the physical properties and performance of the compositions of this disclosure.

If present, the additive(s) may be added to the organic sulfur acid-free composition in an amount in the range of between about 0.1% by weight to about 30% by weight, based on the total weight of the organic sulfur acid-free composition. In further embodiments, the additive(s) may be added to the organic sulfur acid-free composition in an amount in the range of between about 2% by weight to about 20% by weight, or between about 5% by weight to about 15% by weight, based on the total weight of the organic sulfur acid-free composition.

The organic sulfur acid-free composition according to the present disclosure may be prepared by known methods, for example, by combining the benzoxazine, phenolic compound, nitrogen-containing heterocyclic compound and optional solvent and additives with the aid of known mixing units such as kneaders, stirrers, rollers, in mills or in dry mixers.

It has been surprisingly found that the benzoxazine, phenolic compound and nitrogen-containing heterocyclic compound of the present disclosure, when combined, form an organic sulfur acid-free composition that, upon curing at temperatures lower than generally used, for example at a temperature as low as in the range from 130° C.-140° C., produces a void free cured article ("void free" meaning no gas bubbles in the cured article) that exhibits an excellent balance of thermal, mechanical and physical properties, such as, high glass transition temperature (Tg), low coefficient of thermal expansion, low viscosity, high toughness, high mechanical strength, low water absorption, and flame retardancy.

As noted above, the organic sulfur acid-free composition is particularly suitable for use as a coating, adhesive, sealant, and matrice for the preparation of reinforced composite material, such as prepregs and towpregs, and can also be used in injection molding or extrusion processes.

Thus, in another embodiment, the present disclosure provides an adhesive, sealant, coating or encapsulating system for electronic or electrical components comprising the organic sulfur acid-free composition of the present disclosure. Suitable substrates on which the coating, sealant, adhesive or encapsulating system comprising the organic sulfur acid-free composition may be applied include metal, such as steel, aluminum, titanium, magnesium, brass, stainless steel, galvanized steel; silicates such as glass and quartz; metal oxides; concrete; wood; electronic chip material, such as semiconductor chip material; or polymers, such as polyimide film and polycarbonate. The adhesive, sealant or coating comprising the organic sulfur acid-free composition may be used in a variety of applications, such as in industrial or electronic applications.

In another embodiment, the present disclosure provides a cured product produced by curing the organic sulfur acid-free composition at a temperature of about 130° C.-140° C. In still another embodiment, the present disclosure provides a cured product comprising bundles or layers of fibers infused with the organic sulfur acid-free composition.

The organic sulfur acid-free composition (and prepregs or towpregs prepared therefrom) is particularly useful in the manufacture and assembly of composite parts for aerospace and automotive applications, bonding of composite and metal parts, core and core-fill for sandwich structures and composite surfacing.

Another aspect of the present disclosure is the use of the organic sulfur acid-free composition in the process of preparing castings, prepregs or laminates and infusion systems.

Thus, in another aspect, there is provided a method for producing a composite article including the steps of: (i) providing a layer or bundle of reinforcement fibers; (ii) providing the organic sulfur acid-free composition of the present disclosure; (iii) contacting the reinforcement fibers with the organic sulfur acid-free composition to coat and/or impregnate the reinforcement fibers; and (iv) curing the coated and/or impregnated reinforcement fibers at a temperature of least about 80° C.

Coating and/or impregnation may be affected by either a wet method or hot melt method. In the wet method, the organic sulfur acid-free composition is first dissolved in a solvent to lower viscosity, after which coating and/or impregnation of the reinforcement fibers is effected and the solvent evaporated off using an oven or the like. In the hot melt method, coating and/or impregnation may be effected by directly coating and/or impregnating the reinforcement fibers with the organic sulfur acid-free composition which has been heated to reduce its viscosity, or alternatively, a coated film of the organic sulfur acid-free composition may first be produced on release paper or the like, and the film placed on one or both sides of the reinforcement fibers and heat and pressure applied to effect coating and/or impregnation of the organic sulfur acid-free composition.

According to another aspect, there is provided a method for producing a flame retarded composite article in a RTM system. The process includes the steps of: a) introducing a fiber preform comprising reinforcement fibers into a mold;

b) injecting the organic sulfur acid-free composition into the mold, c) allowing the organic sulfur acid-free composition to impregnate the fiber preform; and d) heating the resin impregnated preform at a temperature of least about 80° C., in some embodiments at least about 100° C. to about 180° C. for a period of time to produce an at least partially cured solid article; and e) optionally subjecting the partially cured solid article to post curing operations to produce the flame retarded composite article.

In an alternative embodiment, the present disclosure provides a method for forming a flame retarded composite article in a VaRTM system. The process includes the steps of a) introducing a fiber preform comprising reinforcement fibers into a mold; b) injecting the organic sulfur acid-free composition into the mold; c) reducing the pressure within the mold; d) maintaining the mold at about the reduced pressure; e) allowing the organic sulfur acid-free composition to impregnate the fiber preform; and f) heating the resin impregnated preform at a temperature of at least about 80° C., and in some embodiments at least about 90° C. to about 180° C. for a period of time to produce an at least partially cured solid article; and g) optionally subjecting the at least partially cured solid article to post curing operations to produce the flame retarded composite article.

EXAMPLES

Unless otherwise specified, all parts in the following examples are parts by weight.

Comparative Example #1

100 parts of XU 35710 benzoxazine resin and 1 part of DY 070 (1-methylimidazole) were melt blended at around 90° C. for 5 min and a well homogeneous mixture was obtained. The reactivity of the blend was measured by DSC at heating rate of 10° C./min.

Comparative Example #2

100 parts of XU 35710 benzoxazine resin and 2 parts of DY 070 were melt blended at around 90° C. for 5 min and a well homogeneous mixture was obtained. The reactivity of the blend was measured by DSC at heating rate of 10° C./min.

Comparative Example #3

100 parts of XU 35710 benzoxazine resin and 20 parts of Durite SD-1702 novolac were dissolved in acetone. The solvent was then removed by vacuum while heating from room temperature slowly up to 110° C. The reactivity of the final mixture was measured by DSC at heating rate of 10° C./min.

Example #1

100 parts of XU 35710 benzoxazine resin, 20 parts of Durite SD-1702 novolac and 1 part of DY 070 were dissolved in acetone. The solvent was then removed by vacuum while heating from room temperature slowly up to 110° C. The reactivity of the final mixture was measured by DSC at heating rate of 10° C./min.

Example #2

100 parts of XU 35710 benzoxazine resin, 20 parts of Durite SD-1702 novolac, and 2 parts of DY 070 were dissolved in acetone. The solvent was then removed by vacuum while heating from room temperature slowly up to 110° C. The reactivity of the final mixture was measured by DSC at heating rate of 10° C./min.

Example #3

100 parts of XU 35710 benzoxazine resin, 20 parts of Durite SD-1702 novolac and 2 parts of imidazole were dissolved in acetone. The solvent was then removed by vacuum while heating from room temperature slowly up to 110° C. The reactivity of the final mixture was measured by DSC at heating rate of 10° C./min.

As shown in Table 1 below, Examples #1, #2 and #3 show much lower onset reaction temperatures than Comparative Examples #1, #2 and #3 and as well as the neat benzoxazine resin.

TABLE 1

| | Reactivity of Compositions | | | | | | |
|---|---|---|---|---|---|---|---|
| | Examples # | | | | | | |
| | XU 35710 (neat) | Comp. #1 | Comp. #2 | Comp. #3 | Ex. #1 | Ex. #2 | Ex. #3 |
| DSC onset, ° C. | 212 | 176 | 173 | 162 | 136 | 125 | 126 |
| DSC peak, ° C. | 228 | 205 | 196 | 195 | 188 | 188 | 188 |

Comparative Example #4

100 parts of XU 35710 benzoxazine resin and 30 parts of Durite SD-1702 novolac were mixed with 51 parts acetone until all components were well dissolved. A solvent based prepreg was made using the composition and a 7781 glass cloth. The material was B-staged at 130° C. for 3 min. Two to eight layers were then press cured at different conditions. Properties of the prepreg and final laminate are listed in Table 2.

Comparative Example #5

Glass laminate XU 35710 benzoxazine resin with glass 7781 was prepared by RTM. The benzoxazine resin was injected at around 100° C. The mold was then preheated to around 100° C. and held under vacuum. The benzoxazine resin was injected under pressure at around 95° C. After the mold was filled, the exit was closed, and the laminate was heated and cured for 1 hour at 150° C.+2 hours at 177° C. before cooling and demolding. The final $T_g$ of the laminate based on E' of DMA was 137° C.

Example #4

100 parts of XU 35710 benzoxazine resin, 30 parts of Durite SD-1702 novolac and 2 parts of imidazole were mixed with 51 parts acetone until all components were well dissolved. A solvent based prepreg was made with 7781 glass cloth. The material was B-staged at 130° C. for 3 min. Two to eight layers were then press cured at different conditions. Properties of the prepreg and final laminate are listed in Table 2. The final $T_g$ of the laminate based on E' of DMA was 137° C.

Example #5

100 parts of XU 35710 benzoxazine resin, 30 parts of Durite SD-357B novolac and 2 parts of imidazole were mixed with 51 parts acetone until all components are well dissolved. A solvent based prepreg was made with 7781 glass cloth. The material was B-staged at 1300 C for 3 min. Two to eight layers were then press cured at different condition. Properties of the prepreg and final laminate are listed in Table 2.

TABLE 2

Prepreg $T_g$ Build-Up Under Different Cure Conditions

| Examples # | Comparative #4 | Example #4 | Example #5 |
|---|---|---|---|
| Prepregging condition: 130° C./3 min | | | |
| Prepreg DSC onset/peak | 167/196 | 139/199 | 139/198 |
| Press curing condition: 130° C. (265° F.)/90 min at 20 psi | | | |
| Tg by DSC, ° C. | 102 | 109 | 117 |
| Tg by DMA (E'), ° C. | 115 | 123 | 129 |
| Press curing condition: 145° C. (293° F.)/60 min at 20 psi | | | |
| Tg by DSC, ° C. | 121 | 134 | 127 |
| Tg by DMA (E'), ° C. | 129 | 134 | 139 |
| Post cured at 160° C./1 h | | | |
| Tg by DSC, ° C. | 137 | 147 | 138 |
| Tg by DMA (E'), ° C. | 138 | 138 | 144 |

As shown in the Table 2, Examples #4 and #5 have much faster $T_g$ build-up than Comparative Example #4 and low cure temperature. No sacrifices in the final $T_g$ were found for Examples #4 or #5 as compared to Comparative Examples #4 and #5. As shown in Table 3, the FST performances of all Examples meet FAR 25.853 requirements.

TABLE 3

FST Performance of 2 Layer Glass Laminate

| Formulation | Test Method | Specification | Comp. #4 | Example #4 | Example #5 |
|---|---|---|---|---|---|
| Fibre volume content, % | | | 55 | 52 | 50 |
| Flammability - 60 second vertical burn | FAR 25.853(a) | <15 seconds | 0.0 | 0.0 | 0.0 |
| Extinguish Time - Burn Length - Drip Extinguish Time - | | <6 inches | 4.3 | 5.5 | 5.2 |
| | | <3 seconds | 0.0 | 0.0 | 0.0 |
| Smoke Density Spec. Optical Density - | FAR 25.853(d) | <200 (Ds) | 9.2 | 8.3 | 14.5 |
| Heat release Total Heat Release - Peak Heat Release - | FAR 25.853(d) | <65 kW · min per m² | 22 | 38 | 30 |
| | | <65 kW/m² | 46 | 51 | 41 |
| Toxicity | BSS 7239 | HCN - <150. | <5 | <5 | <5 |
| | | CO - Ref. | 45 | 101 | 56 |
| | | NOx - <100. | 8 | 11 | 7 |
| | | SO2 - <100. | <5 | <5 | <5 |
| | | HF - <200. | <5 | <5 | <5 |
| | | HCL - <500. | <5 | <5 | <5 |

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. An organic sulfur acid-free composition comprising:
(a) a benzoxazine compound comprising
(i) a compound of the formula

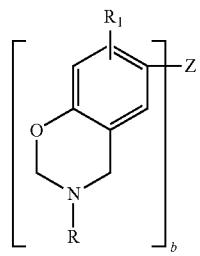

(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group or a $C_3$-$C_8$ cycloalkyl group; each $R_1$ is independently hydrogen, a $C_1$-$C_{20}$ alkyl group, a $C_2$-$C_{20}$ alkenyl group or a $C_6$-$C_{20}$ aryl group; and Z is a direct bond when b=2, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O, (ii) a compound having the formula

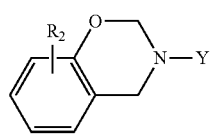

(2)

where Y is a $C_1$-$C_{20}$ alkyl group, a $C_2$-$C_{20}$ alkenyl group or substituted or unsubstituted phenyl; and $R_2$ is hydrogen, halogen, a $C_1$-$C_{20}$ alkyl group or a $C_2$-$C_{20}$ alkenyl group, or (iii) a compound having the formula

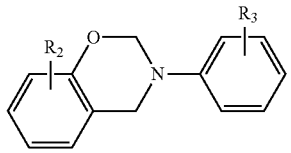
(2a)

where $R_2$ is a $C_1$-$C_{20}$ alkyl group or a $C_2$-$C_{20}$ alkenyl group, each of which is optionally substituted or interrupted by one or more O, N, S, C=O, COO, NHC=O or a $C_6$-$C_{20}$ aryl group; and $R_3$ is hydrogen, a $C_1$-$C_{20}$ alkyl group or a $C_2$-$C_{20}$ alkenyl group, each of which is optionally substituted or interrupted by one or more O, N, S, C=O, COOH, NHC=O or a $C_6$-$C_{20}$ aryl group;

(b) a phenolic compound comprising (i) a monofunctional compound having the formula

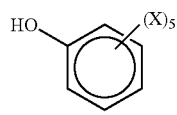
(4)

where each X is independently hydrogen, halogen, a hydrocarbyl group having from 1 to 20 carbon atoms or a hydrocarbyloxy group having from 1 to 20 carbon atoms, (ii) a difunctional compound having the formula

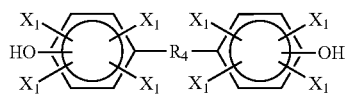
(5)

where each $X_1$ is independently hydrogen, a $C_1$-$C_{20}$ alkyl group, an alkoxy group, an alloxy group or a halogen; and $R_4$ is a direct bond, a $C_1$-$C_{20}$ alkyl group,

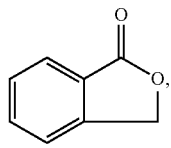

—O—, —S—, —S—S—, —S(=O)—, —(O=)S(=O)—, —C(=O)—, —NHC(=O)— or NHC(=O)—O—, or (iii) a multifunctional phenolic compound comprising a novolac resin; and (c) a nitrogen-containing heterocyclic compound comprising an imidazole, imidazolidine, imidazoline, oxazole, pyrrole, thiazole, pyridine, pyrazine, morpholine, pyridazine, pyrimidine, pyrrolidine, pyrazole, phthalozine, quinoline, purine, indazole, indole, pyrroline, indoline, piperidine, piperazine or a combination thereof.

2. The organic sulfur acid-free composition of claim 1 wherein the benzoxazine compound is a compound of the formula

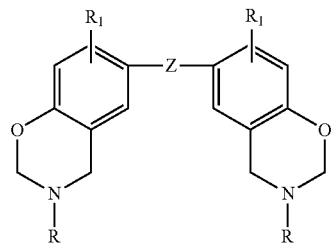
(1a)

where Z is selected from a direct bond, $CH_2$, $C(CH_3)_2$, C=O, O, S, S=O, O=S=O and

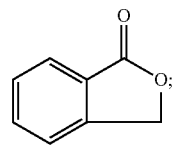

each R is independently hydrogen, a $C_1$-$C_{20}$ alkyl group, an allyl group or a $C_6$-$C_{14}$ aryl group; and each $R_1$ is independently hydrogen, a $C_1$-$C_{20}$ alkyl group, a $C_2$-$C_{20}$ alkenyl group or a $C_6$-$C_{20}$ aryl group.

3. An organic sulfur acid-free composition comprising:

(a) about 10% by weight to about 98% by weight of a benzoxazine resin comprising (i) a compound of the formula

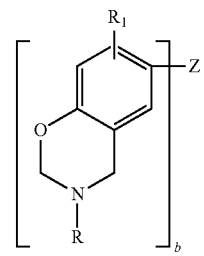
(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group or a $C_3$-$C_8$ cycloalkyl group; each $R_1$ is independently hydrogen, a $C_1$-$C_{20}$ alkyl group, a $C_2$-$C_{20}$ alkenyl group or a $C_6$-$C_{20}$ aryl group; and Z is a direct bond when b=2, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O, (ii) a compound having the formula

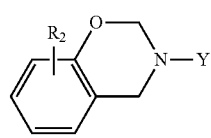

(2)

where Y is a $C_1$-$C_{20}$ alkyl group, a $C_2$-$C_{20}$ alkenyl group or substituted or unsubstituted phenyl; and $R_2$ is hydrogen, halogen, a $C_1$-$C_{20}$ alkyl group or a $C_2$-$C_{20}$ alkenyl group, or (iii) a compound having the formula

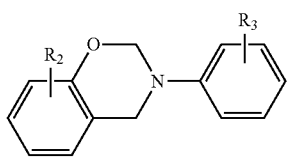

(2a)

where $R_2$ is a $C_1$-$C_{20}$ alkyl group or a $C_2$-$C_{20}$ alkenyl group, each of which is optionally substituted or interrupted by one or more O, N, S, C=O, COO, NHC=O or a $C_6$-$C_{20}$ aryl group; and $R_3$ is hydrogen, a $C_1$-$C_{20}$ alkyl group or a $C_2$-$C_{20}$ alkenyl group, each of which is optionally substituted or interrupted by one or more O, N, S, C=O, COOH and NHC=O, or a $C_6$-$C_{20}$ aryl group;

(b) greater than 3% by weight to about 60% by weight of a phenolic compound comprising (i) a monofunctional compound having the formula

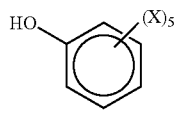

(4)

where each X is independently hydrogen, halogen, a hydrocarbyl group having from 1 to 20 carbon atoms or a hydrocarbyloxy group having from 1 to 20 carbon atoms, (ii) a difunctional compound having the formula

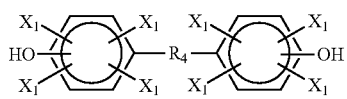

(5)

where each $X_1$ is independently hydrogen, a $C_1$-$C_{20}$ alkyl group, an alkoxy group, an alloxy group or a halogen; and $R_4$ is a direct bond, a $C_1$-$C_{20}$ alkyl group,

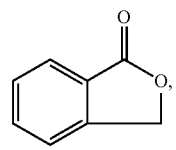

—O—, —S—, —S—S—, —S(=O), —(O=)S(=O)—, —C(=O)—, —NHC(=O)— or NHC(=O)—O—, or (iii) a multifunctional phenolic compound comprising a novolac resin; and (c) about 0.01% by weight to about 30% by weight of a nitrogen-containing heterocyclic compound comprising an imidazole, imidazolidine, imidazoline, oxazole, pyrrole, thiazole, pyridine, pyrazine, morpholine, pyridazine, pyrimidine, pyrrolidine, pyrazole, phthalozine, quinoline, purine, indazole, indole, pyrroline, indoline, piperidine, piperazine or a combination thereof, wherein the % by weight is based on the total weight of composition.

4. A cured article comprising the organic sulfur acid-free composition of claim 1.

5. A cured article comprising bundles or layers of fibers infused with the organic sulfur acid-free composition of claim 1.

6. A method for producing a composite article comprising the steps of: (i) providing a layer or bundle of reinforcement fibers; (ii) providing the organic sulfur acid-free composition of claim 1; (iii) contacting the reinforcement fibers with the organic sulfur acid-free composition to coat and/or impregnate the reinforcement fibers; and (iv) curing the coated and/or impregnated reinforcement fibers at a temperature of at least about 80° C.

\* \* \* \* \*